United States Patent [19]

Itoh et al.

[11] Patent Number: 5,141,831
[45] Date of Patent: Aug. 25, 1992

[54] ELECTROPHOTOGRAPHIC PHOTORECEPTOR

[75] Inventors: Akira Itoh; Hideki Nagamura; Hideya Arisue, all of Tsukuba, Japan

[73] Assignee: Mitsubishi Paper Mills Limited, Tokyo, Japan

[21] Appl. No.: 565,239

[22] Filed: Aug. 10, 1990

[30] Foreign Application Priority Data

Aug. 15, 1989 [JP] Japan .................... 1-210430
Aug. 17, 1989 [JP] Japan .................... 1-211877

[51] Int. Cl.$^5$ ............................................. G03G 5/09
[52] U.S. Cl. ................................. 430/59; 430/76; 430/77
[58] Field of Search .................... 430/73, 74, 75, 76, 430/77

[56] References Cited

U.S. PATENT DOCUMENTS 3,579,331 5/1971 Mee et a.l. ................. 430/76
3,798,031 3/1974 Janssens et al. ............. 430/76
4,477,550 10/1984 Horie et al. ................. 430/77

FOREIGN PATENT DOCUMENTS 3236477 4/1983 Fed. Rep. of Germany .
3331259 3/1984 Fed. Rep. of Germany .

Primary Examiner—John Goodrow
Attorney, Agent, or Firm—Cushman, Darby & Cushman

[57] ABSTRACT

The present invention provides an electro-photographic photoreceptor which is high in sensitivity and endurance which comprises an electroconductive support and, provided thereon, a photosensitive layer which contains a compound represented by the following formula [I]:

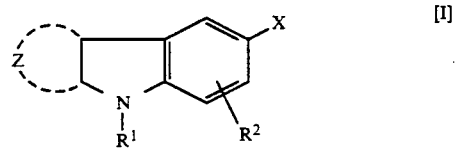

wherein $R^1$ and $R^2$ each represents a hydrogen atom or an alkyl, aralkyl or aryl group which may have substituent: X represents

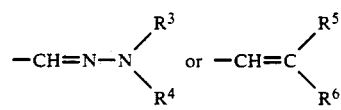

in which $R^3$ and $R^4$ each represents an alkyl, aralkyl or aryl group which may have substituent and $R^5$ and $R^6$ each represents a hydrogen atom or an alkyl, aralkyl or aryl group which may have substituent and $R^5$ and $R^6$ may link to each other to form a ring; and Z represents a group of atoms necessary for forming a saturated 5-8 membered ring together with two carbon atoms of the indoline ring.

10 Claims, No Drawings

ELECTROPHOTOGRAPHIC PHOTORECEPTOR

BACKGROUND OF THE INVENTION

The present invention relates to an electro-photographic photoreceptor which contains a novel hydrazone or styryl compound.

Hitherto, inorganic photoconductive substances such as selenium, cadmium sulfide, zinc oxide and silicon have been known for photoreceptors of electrophotographic system and widely studied and have been put to practical use. Recently, organic photoconductive materials have also been intensively studied as electrophotographic photoreceptors and some of them have been practically used.

In general, inorganic materials are unsatisfactory, for example, selenium photoreceptors have problems such as low heat stability, deterioration of characteristics due to crystallization and difficulty in production and cadmium sulfide photoreceptors have problems in moisture resistance, endurance and disposal of industrial waste. On the other hand, organic materials have advantages such as good film-formability, excellent flexibility, light weight, high transparency and easy designing of photoreceptors for wavelength of wide region by suitable sensitization. Thus, organic materials have increasingly attracted public attention.

Photoreceptors used in electrophotographic process are required to possess the following fundamental properties, namely, (1) high chargeability for corona discharge in the dark place, (2) less leakage of the resulting charge in the dark place (dark decay), (3) rapid release of charge by irradiation with light (light decay), and (4) less residual charge after irradiation with light.

Extensive research has been made on photoconductive polymers as organic photoconductive substances including polyvinylcarbazole and others, but these are not necessarily sufficient in film-formability, flexibility and adhesion and besides these cannot be said to have sufficiently possess the above-mentioned fundamental properties as photoreceptor.

On the other hand, in case of organic low molecular photoconductive compounds, photoreceptors excellent in film-formability, adhesion, flexibility and other mechanical strengths can be obtained therefrom by selection of binders, etc. used for production of photoreceptors, but it is difficult to find compounds suitable to keep the characteristic of high sensitivity.

In order to improve these problems, there has been made development of organic photoreceptors having higher sensitivity by bearing the carrier generating function and the carrier transporting function by different substances. Characteristics of such photoreceptor called double-layered structure is that materials suitable for respective functions can be selected from wide variety of materials and photoreceptors having optional performances can be easily produced and thus intensive research has been made on such photoreceptors.

As explained above, many improvements have been made in production of electrophotographic photoreceptors, but those which meet the requirements for fundamental properties mentioned above and high endurance have not yet been obtained.

SUMMARY OF THE INVENTION

The object of the present invention is to provide an electrophotographic photoreceptor having high sensitivity and high endurance and especially to provide a photoreceptor which is high in charge characteristics, shows substantially no reduction of sensitivity after repeated use and is stable in charge potential.

DESCRIPTION OF THE INVENTION

As a result of research conducted by the inventors on photoconductive substances having high sensitivity and high endurance, it has been found that the novel compounds represented by the following formula [I] are effective and the present invention has been accomplished.

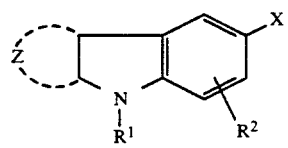

(wherein $R^1$ and $R^2$ each represents a hydrogen atom or an alkyl, aralkyl or aryl group which may have substituent: X represents

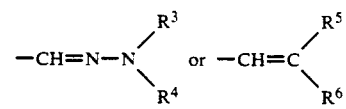

in which $R^3$ and $R^4$ each represents an alkyl, aralkyl or aryl group which may have substituent and $R^5$ and $R^6$ each represents a hydrogen atom or an alkyl, aralkyl or aryl group which may have substituent and $R^5$ and $R^6$ may link to each other to form a ring; and Z represents a group of atoms necessary for forming a saturated 5–8 membered ring together with two carbon atoms of the indoline ring).

Examples of $R^1$ and $R^2$ are hydrogen atom, alkyl groups such as methyl group, ethyl group and propyl group, aralkyl groups such as benzyl group, methylbenzyl group, chlorobenzyl group, β-phenylethyl group, and α-naphthylmethyl group, and aryl groups such as phenyl group, methoxyphenyl group, tolyl group, chlorophenyl group, and naphthyl group. Examples of $R^3$, $R^4$, $R^5$ and $R^6$ are hydrogen atom, alkyl groups such as methyl group, ethyl group, and propyl group, aralkyl groups such as benzyl group, methylbenzyl group chlorobenzyl group, β-phenyl-ethyl group, and α-naphthylmethyl group, and aryl groups such as phenyl group, methoxyphenyl group, tolyl group, chlorophenyl group, and naphthyl group. Examples of Z are as shown in the compounds enumerated hereinafter.

The compounds represented by the above formula can be prepared by the following preparation examples.

PREPARATION EXAMPLE 1

[Preparation of compound (3) enumerated hereinafter]

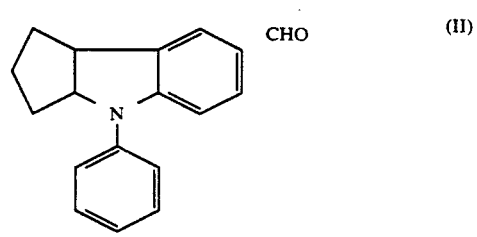

Acetic acid (0.2 ml) was added to an ethanolic solution (20 ml) of aldehyde compound (2.63 g) of the above formula [II] and phenylmethylhydrazine (1.22 g), followed by refluxing for 2 hours. The product was filtrated and recrystallized from ethyl acetate to obtain 2.15 g of compound (3).

Melting point: 134.0°–135.3° C.

NMR (δ, ppm, CDCl$_3$): 1.5–2.2(m, 6H), 3.43(S, 3H), 3.91(m, 1H), 4.85(m, 1H), 6.9–7.1(m, 3H), 7.3–7.5(m, 9H), 7.54(S, 1H), 7.6(S, 1H).

PREPARATION EXAMPLE 2

[Preparation of compound (35) enumerated hereinafter]

Potassium t-butoxide (1.46 g) was added to 1,2-dimethoxyethane solution (25 ml) of the aldehyde compound (3.31 g) of the above formula [II] and diethylbenzhydryl phosphonate (3.95 g) at 0° C., followed by stirring for 20 minutes at the same temperature and for 1 hour at room temperature. The reaction product was introduced into water and extracted with ethyl acetate. The extract was purified by silica gel column chromatography to obtain 3.63 g of compound (35).

Melting point: 131.1°–132.7° C.

NMR (δ, ppm, CDCl$_3$): 1.5–2.1(m, 6H), 3.74(m, 1H), 4.83(m, 1H), 6.84(s, 1H), 6.9–7.1(m, 4H), 7.3–7.6(m, 15H).

Examples of the compounds represented by the formula [I] are shown below, it being understood that the present invention is never limited to these examples.

(1)

(2)

(3)

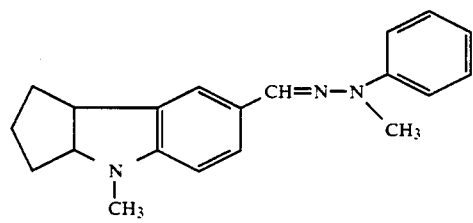

(4)

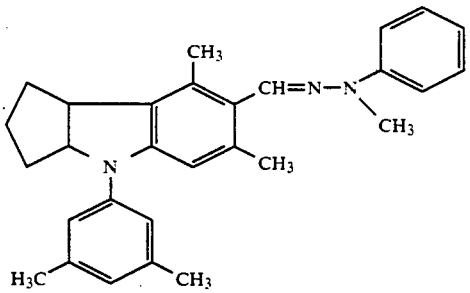

(5)

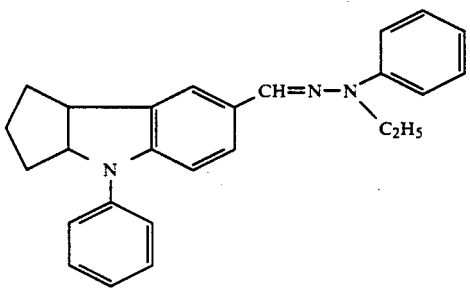

(6)

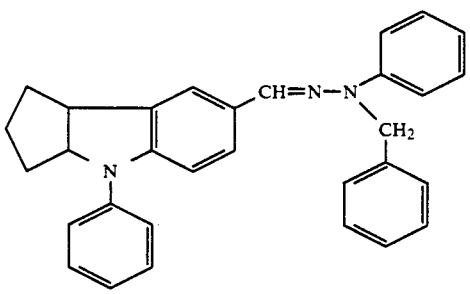

(7)

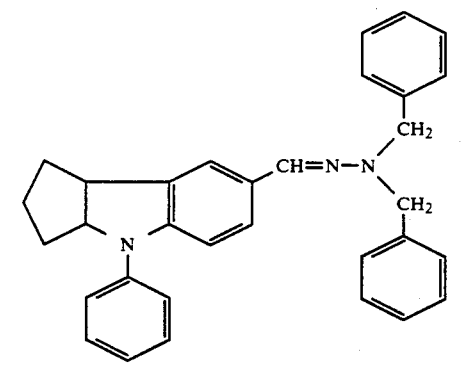

(8)

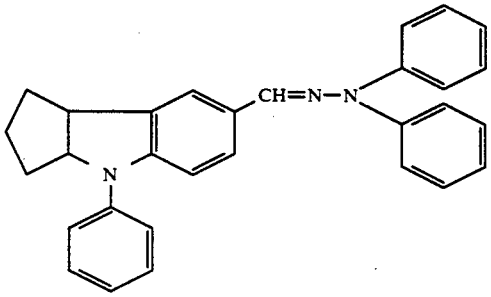

-continued
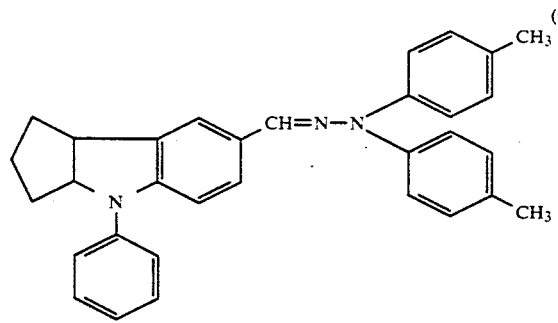
(9)
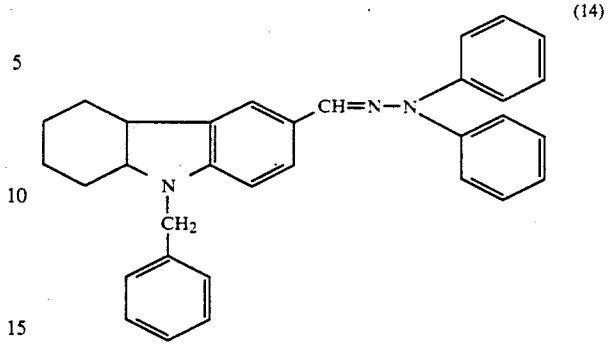
(14)
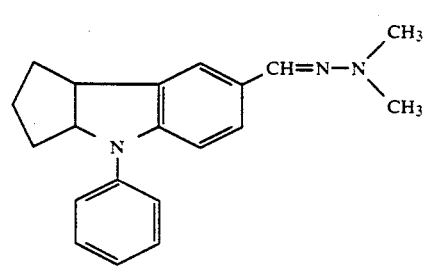
(10)
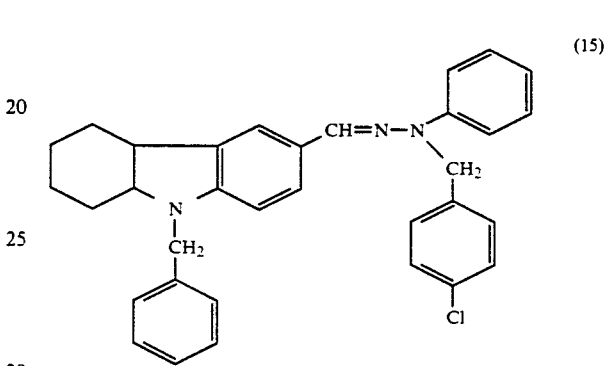
(15)
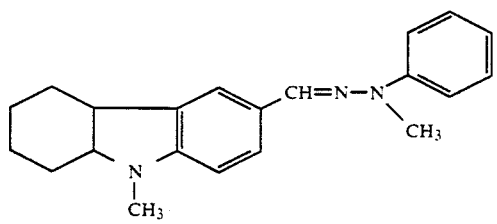
(11)
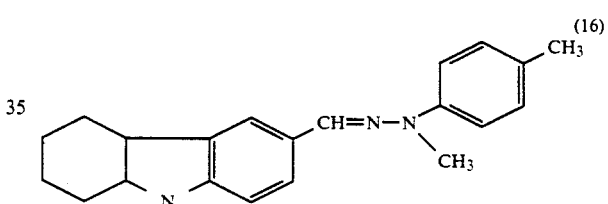
(12)
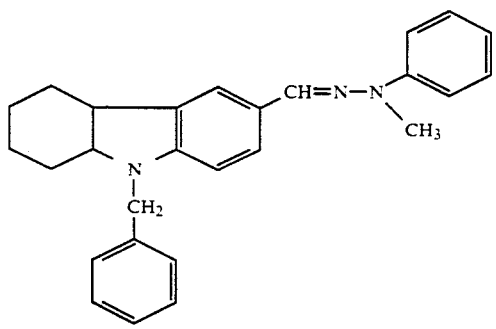
(16)
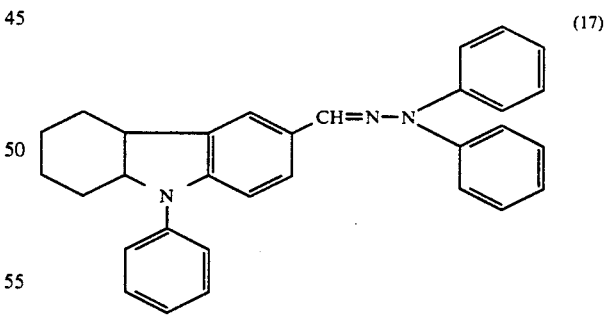
(17)
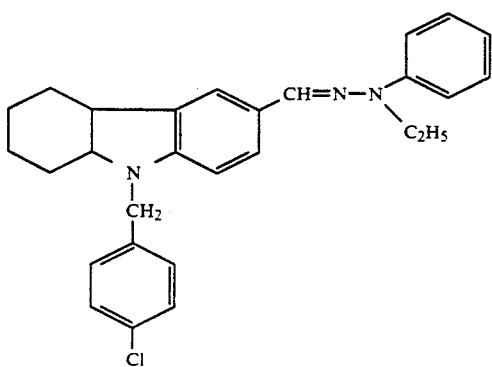
(13)
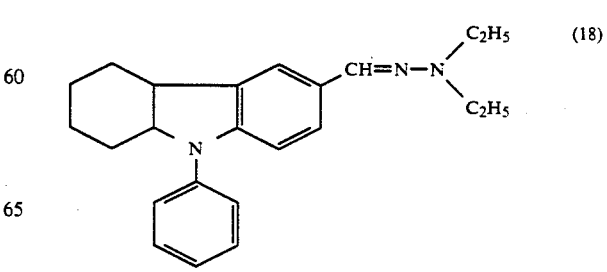
(18)

-continued
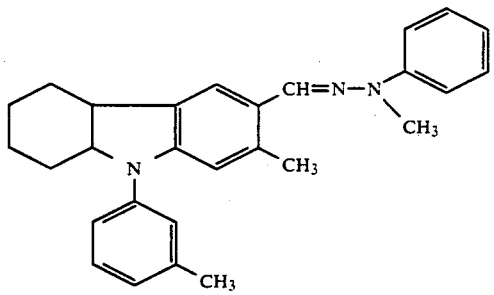 (19)
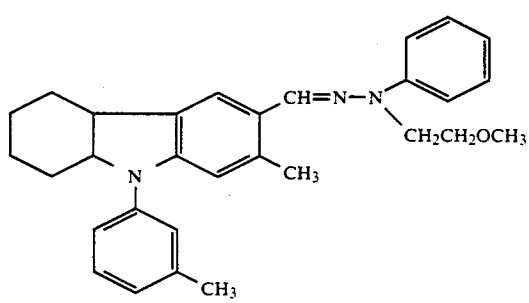 (20)
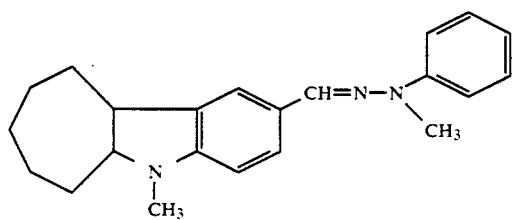 (21)
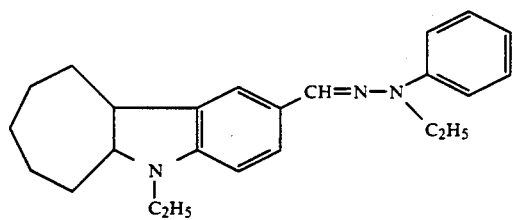 (22)
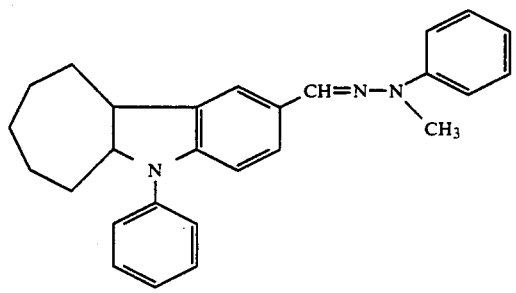 (23)
-continued
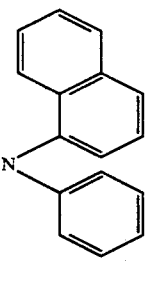 (24)
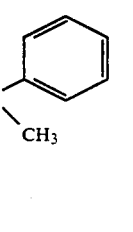 (25)
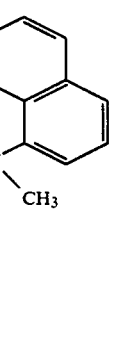 (26)
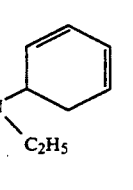 (27)
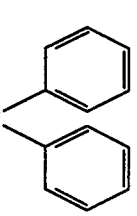 (28)

-continued
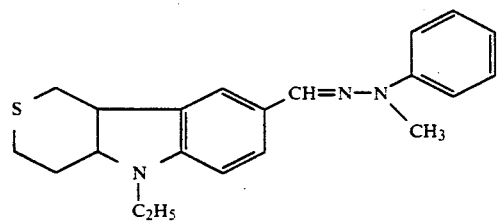 (29)
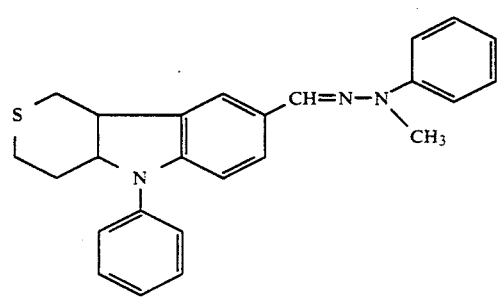 (30)
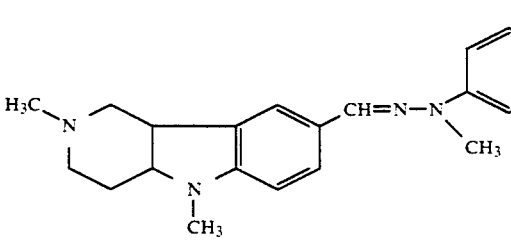 (31)
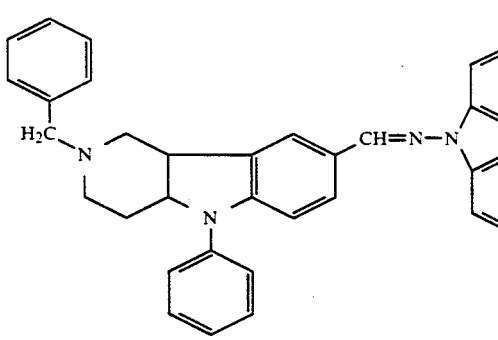 (32)
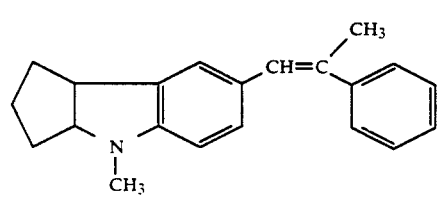 (33)
-continued
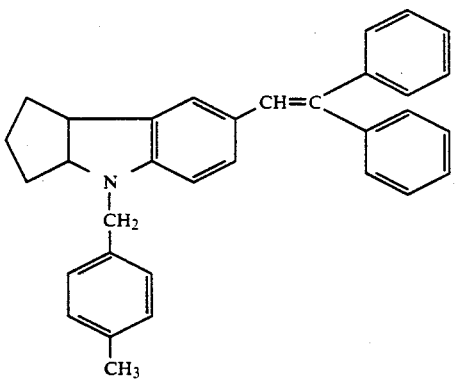 (34)
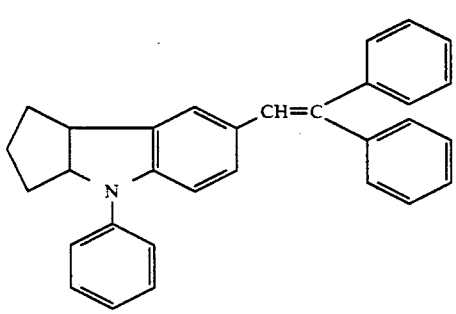 (35)
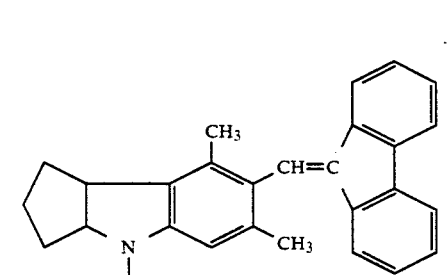 (36)
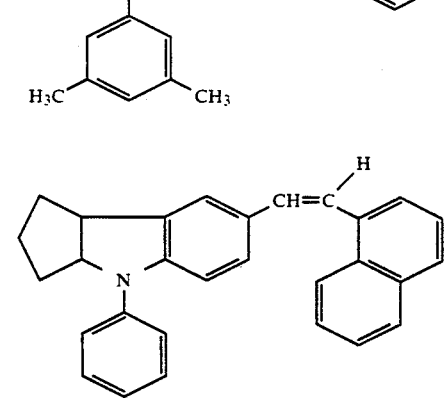 (37)
(38)

-continued
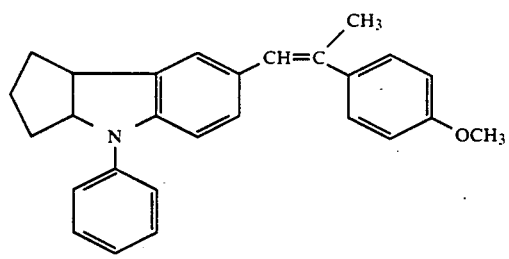 (39)
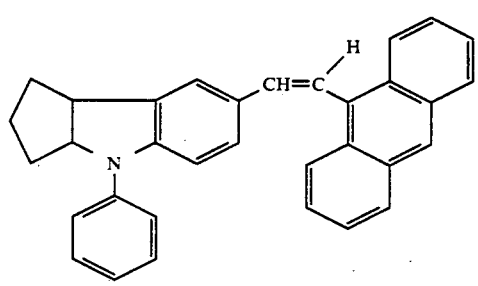 (40)
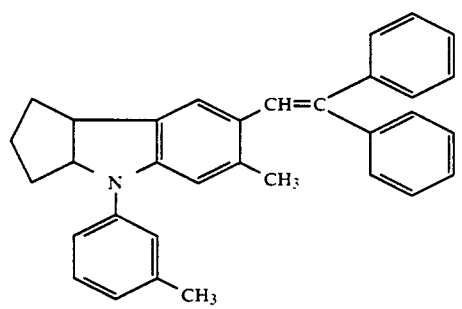 (41)
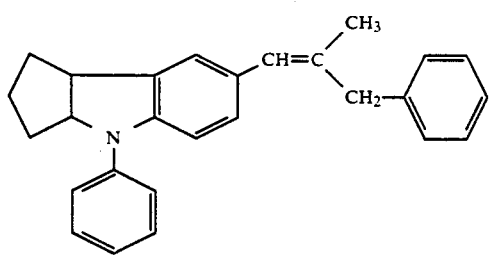 (42)
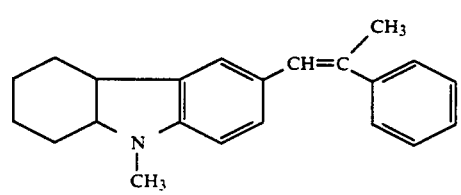 (43)
-continued
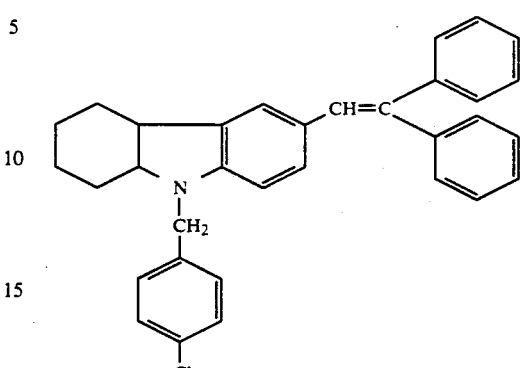 (44)
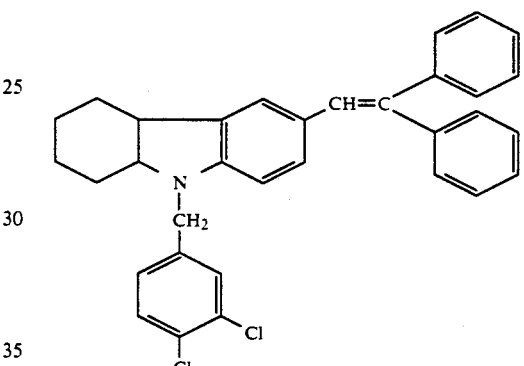 (45)
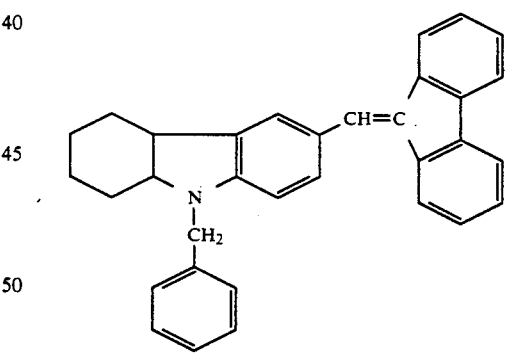 (46)
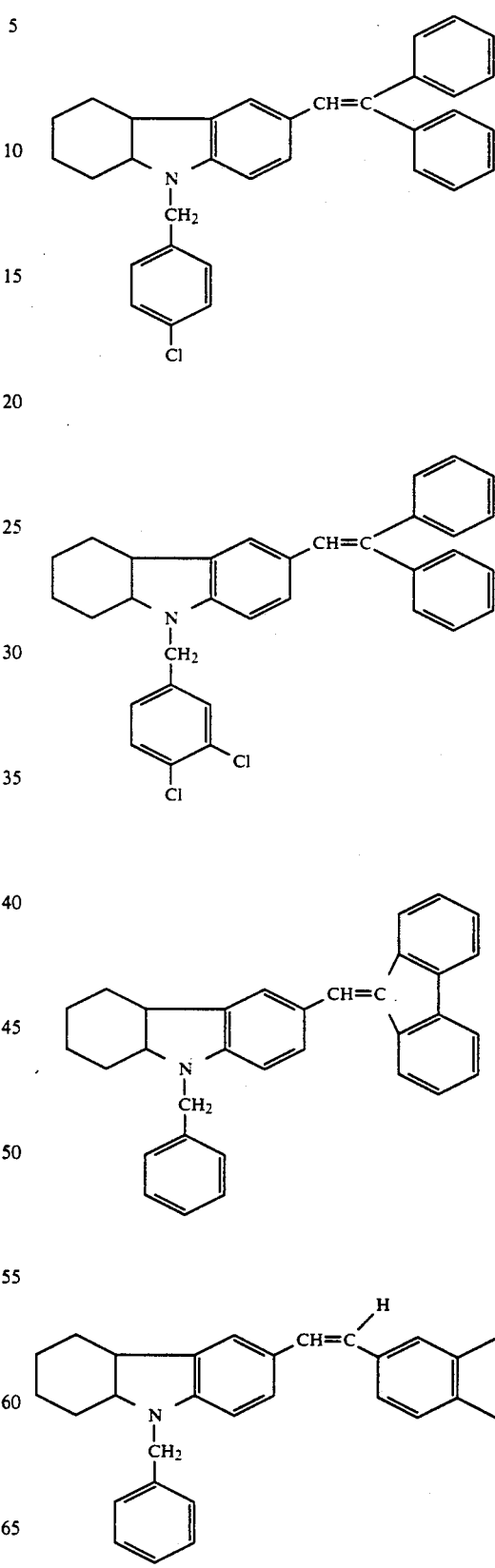 (47)

-continued
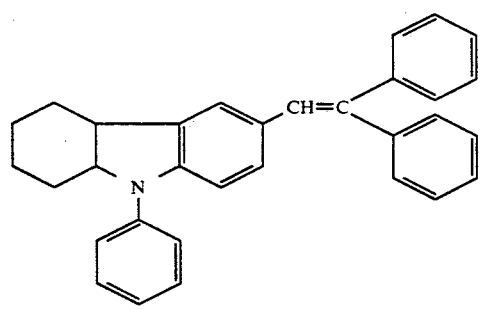
(48)
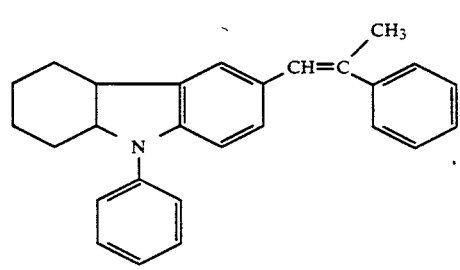
(49)
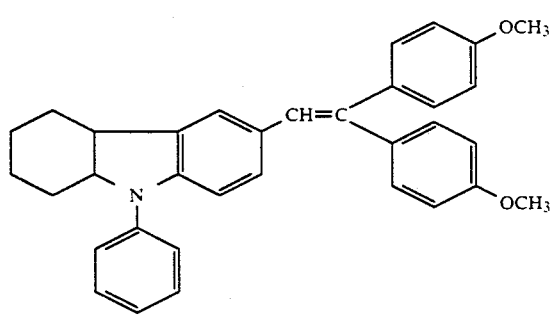
(50)
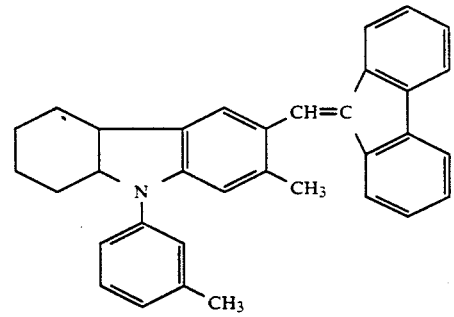
(51)
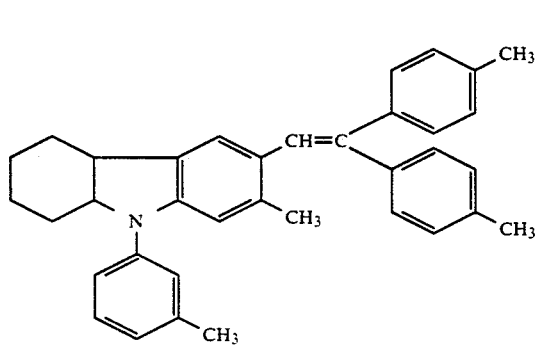
(52)
-continued
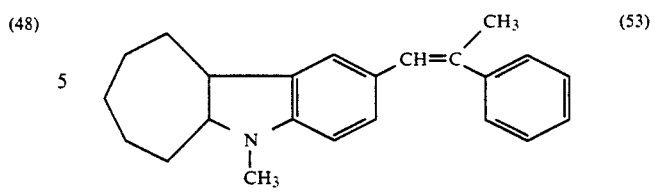
(53)
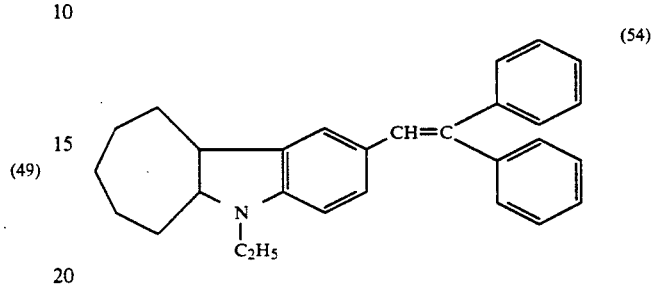
(54)
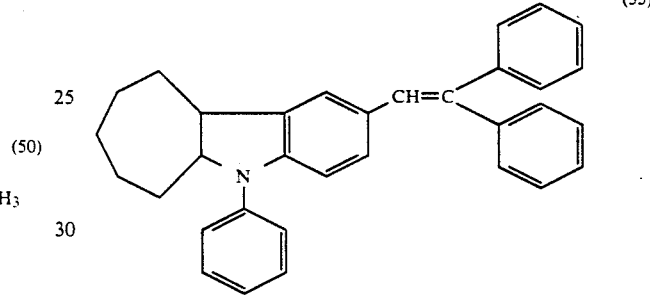
(55)
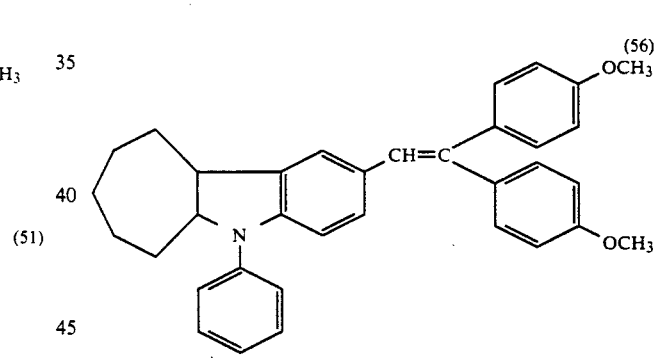
(56)
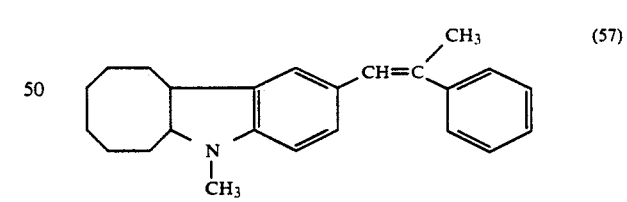
(57)
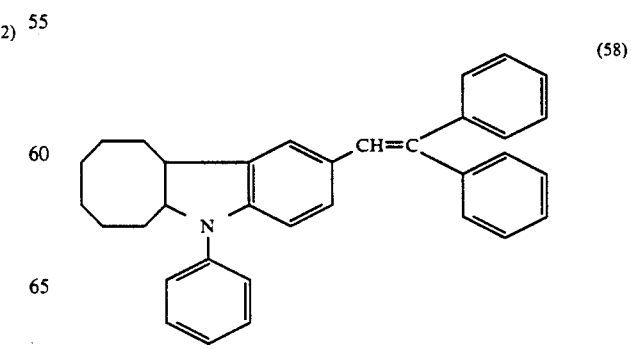
(58)

-continued

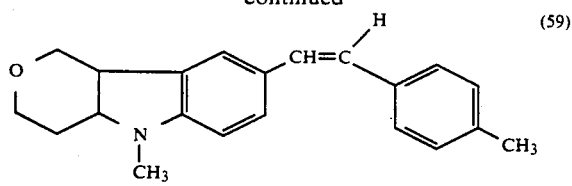
(59)

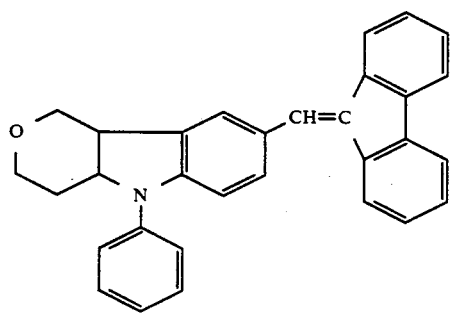
(60)

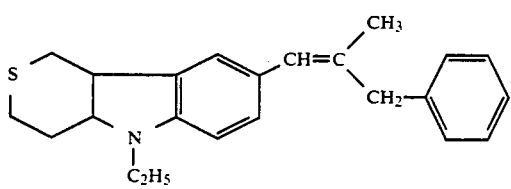
(61)

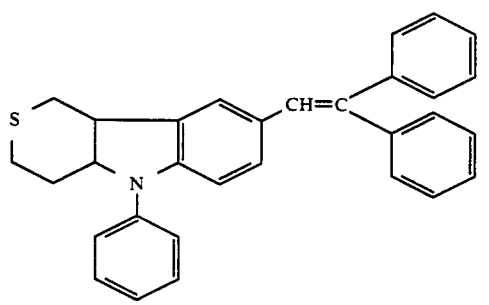
(62)

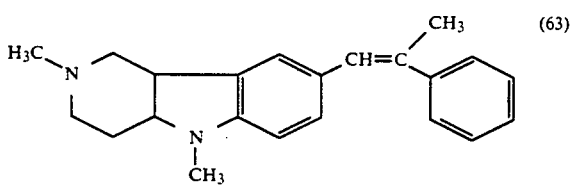
(63)

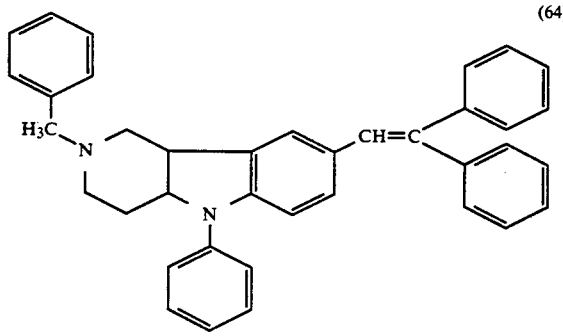
(64)

The electrophotographic photoreceptor of the present invention is obtained by containing at least one of hydrazone or styryl compounds represented by the above formula [I] and it has excellent properties.

Various methods have been known for use of these compounds as electrophotographic photoreceptor.

For example, there are a photoreceptor which comprises a conductive support on which is coated a solution of dispersion of the compound and a sensitizing dye in a binder resin, if necessary, with addition of a chemical sensitizer or an electron attractive compound; a photoreceptor in the form of a double-layered structure comprising a carrier generation layer and a carrier transport layer wherein a carrier generation layer mainly composed of a carrier generation material of high carrier generation efficiency such as dye or pigment is provided on a conductive support and thereon is provided a carrier transport layer comprising a solution or a dispersion of the present compound in a binder resin, if necessary, with addition of a chemical sensitizer or an electron attractive compound; and such double-layered photoreceptor as mentioned above wherein the carrier generation layer and the carrier transport layer are provided in the reverse order. The compound of the present invention can be applied to all of these photoreceptors.

Supports used for preparation of the photoreceptors using the compounds according to the present invention include, for example, metallic drums, metal sheets, and papers, plastic films or belt-like supports which have been subjected to electroconductive treatment.

As film-forming binder resins used for formation of photosensitive layer on the support, mention may be made of various resins depending on fields of application. For example, in case of photoreceptors for use in copying, mention may be made of polystyrene resin, polyvinylacetal resin, polysulfone resin, polycarbonate resin, vinyl acetate-crotonic acid copolymer resin, polyphenylene oxide resin, polyester resin, alkyd resin, polyarylate resin, acrylic resin, methacrylic resin, and phenoxy resin. Among them, polystyrene resin, polyvinylacetal resin, polycarbonate resin, polyester resin, polyarylate resin, and phenol resin are superior in potential characteristics as photoreceptor.

These resins may be used singly or in combination as homopolymers or copolymers.

Amount of these binder resins to be added to the photoconductive compound is 0.2-10, preferably 0.5-5 times the weight of the photoconductive compound. If the amount is less than this range, the photoconductive compound is precipitated in or on the photosensitive layer to cause deterioration in adhesion to the support and if it is more than the range, sensitivity is reduced.

Further, some of the film-forming binder resins are rigid and low in mechanical strengths such as tensile strength, flexural strength and compression strength and in order to improve these properties, plasticity imparting materials can be added.

These materials include, for example, phthalate esters (such as DOP, DBP and DIDP), phosphate esters (such as TCP and TOP), sebacate esters, adipate esters, nitrile rubber, and chlorinated hydrocarbons. If these materials which impart plasticity are added in an amount more than needed, potential characteristics are deteriorated and so they are added preferably in an amount of 20% by weight or less of binder resin.

The sensitizing dyes added to the photosensitive layer include triphenylmethane dyes such as Methyl Violet, Crystal Violet, Ethyl Violet, Night Blue, and Victoria Blue, xanthene dyes such as erythrosine, Rhodamine B, Rhodamine 3B, and Acridine Red B, acridine dyes such as Acridine Orange 2G, Acridine Orange R and Flaveosine, thiazine dyes such as Methylene Blue and Methylene Green, oxazine dyes such as Capri Blue and Meldola's Blue, and further, cyanine dyes, styryl dyes, pyrylium salts, thiapyrylium salts and squarylium salt dyes.

As photoconductive pigments which generate carriers at very high efficiency upon absorption of light in photosensitive layer, mention may be made of phthalocyanine pigments such as metal-free phthalocyanine and phthalocyanine containing various metals or metal compounds, perylene pigments such as peryleneimide and perylenic anhydride, and quinacridone pigments, anthraquinone pigments, and azo pigments.

Among these pigments, bisazo pigments, trisazo pigments and phthalocyanine pigments high in carrier generating efficiency afford high sensitivity and thus provide excellent electrophotographic photoreceptors.

The dye added to photosensitive layer can be used singly as a carrier generation material, but joint use of this dye with the pigment can generate carrier at higher efficiency. Furthermore, inorganic photoconductive materials include selenium, selenium-tellurium alloy, cadmium sulfide, zinc sulfide and amorphous silicon.

In addition to the above-mentioned sensitizers (so-called spectral sensitizers), there may be added sensitizers for further increase of sensitivity (so-called chemical sensitizers).

Such chemical sensitizers include, for example, p-chlorophenol, m-chlorophenol, p-nitrophenol, 4-chloro-m-cresol, p-chlorobenzoylacetanilide, N,N'-diethyl-barbituric acid, 3-(β-oxyethyl)-2-phenyliminothiazolidone, malonic acid dianilide, 3,5,3',5'-tetrachloromalonic acid dianilide, α-naphthol, and p-nitrobenzoic acid.

Furthermore, it is also possible to add some kinds of electron attractive compounds as sensitizers which form a charge transport complex with the hydrazone or styryl compound of the present invention to further enhance the sensitizing effect.

As the electron attractive compounds, mention may be made of, for example, 1-chloroanthraquinone, 1-nitroanthraquinone, 2,3-dichloronaphthoquinone, 3,3-dinitrobenzophenone, 4-nitrobenzalmalononitrile, phthalic anhydride, 3-(α-cyano-p-nitrobenzal)phthalide, 2,4,7-trinitrofluorenone, 1-methyl-4-nitrofluorenone, and 2,7-dinitro-3,6-dimethylfluorenone.

If necessary, antioxidant, curl inhibitor, etc. may also be added to the photoreceptor.

The compound used in the present invention is dissolved or dispersed in a suitable solvent together with the above-mentioned various additives depending on the form of desired photoreceptor, the resulting coating solution is coated on an electroconductive support mentioned above and is dried to obtain a photoreceptor.

As the solvent for coating solution, for example, halogenated hydrocarbons such as chloroform, dichloroethane, trichloroethane, and trichloroethylene, aromatic hydrocarbons such as benzene, toluene, and xylene, and dioxane, tetrahydrofuran, methyl cellosolve, dimethyl cellosolve and methyl cellosolve acetate are used singly or as mixed solvent of two or more of them. If necessary, solvents such as alcohols, acetonitrile, N,N-dimethylformamide, and methyl ethyl ketone may further be added to the above solvents.

The following nonlimiting examples further explain the present invention.

EXAMPLE 1

One part by weight of a pigment represented by the following formula [III] and 1 part by weight of a polyester resin (BYRON 200 manufactured by Toyobo Co., Ltd.) were mixed with 100 parts by weight of tetrahydrofuran and the mixture was dispersed together with glass beads for 2 hours by a paint conditioner.

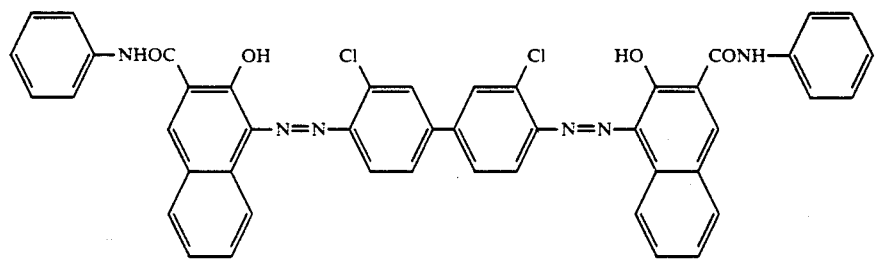

The resulting pigment dispersion was coated on an aluminum-vapor deposited polyester film by an applicator and dried to form a film of carrier generation material of about 0.2 μin film thickness.

Then, the compound (3) exemplified hereinbefore was mixed with a polyarylate resin (U-POLYMER manufactured by Unitika Ltd.) at a weight ratio of 1:1 and a 10% solution of the mixture in dichloroethane as a solvent was prepared. This solution was coated on the film of carrier generation material formed hereabove by an applicator to form a carrier transport layer having a dry film thickness of 20 μ.

Electrophotographic characteristics of the resulting double-layer type electrophotographic photoreceptor were evaluated by an electrostatic recording testing apparatus (SP-428 manufactured by Kawaguchi Denki Seisakusho Co.).

Measuring conditions: Applied voltage −6 KV, static No. 3.

As a result, half decay exposure with white light was 2.1 lux·sec which means very high sensitivity.

In addition, evaluation for repeated use was conducted using this apparatus. Change in charge potential due to repeated uses of 1000 times was measured. The initial potential at the first time was −980 V and that at 1000th time was −950 V. Thus, it can be seen that reduction of potential due to repeated use was small and potential was stable.

EXAMPLE 2

A double-layer type electrophotographic photoreceptor was produced in the same manner as in Example 1 except that compound (35) was used in place of compound (3) and was evaluated in the same manner as in Example 1. Half decay exposure with white light was 2.0 lux·sec which also showed very high sensitivity. Results of test on repeated use were as follows: initial potential at the first time was −930 V and that at 1000th time was −920 V and thus this indicate that reduction of potential due to repeated use was small and potential was stable.

EXAMPLES 3-10

Double-layer type photoreceptors were produced in the same manner as in Example 1 except that compounds shown in Table 1 were used in place of the compound used in Example 1. Half decay exposure E1/2 (lux·sec) and initial potential $V_0$ (volt) were measured under the same measuring conditions as in Example 1 and the results are shown in Table 1. Further, the photoreceptors were subjected to repeated test cycles of 1000 times, one test cycle consisting of charging-removing of potential (removal of potential was carried out by exposing to white light of 400 lux for 1 second) and initial potential $V_0$ (volt) and half decay exposure E1/2 are shown in Table 1.

TABLE 1

| Compound | The 1st time | | The 1000th time | |
|---|---|---|---|---|
| | $V_0$ (volt) | E1/2 (lux · sec) | $V_0$ (volt) | E1/2 (lux · sec) |
| (6) | −850 | 2.1 | −840 | 2.1 |
| (11) | −870 | 2.2 | −850 | 2.2 |
| (26) | −950 | 2.2 | −940 | 2.2 |
| (32) | −910 | 2.2 | −900 | 2.2 |
| (42) | −840 | 2.1 | −830 | 2.1 |
| (44) | −870 | 2.1 | −850 | 2.1 |
| (57) | −910 | 2.2 | −900 | 2.2 |
| (64) | −810 | 2.1 | −800 | 2.1 |

EXAMPLES 11-18

Bisazo pigment of the following structure (IV) was used as a carrier generation material.

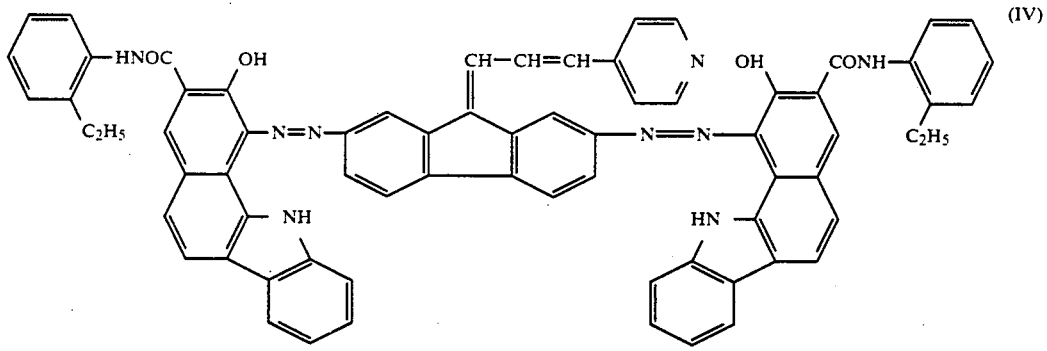

(IV)

That is, 1 part by weight of this pigment and 1 part by weight of a polyester resin (BYRON 200 manufactured by Toyobo Co., Ltd.) were mixed with 100 parts by weight of tetrahydrofuran and the mixture was dispersed by a paint conditioner apparatus together with glass beads for 2 hours. The resulting pigment dispersion was coated on the same support as used in Example 1 by an applicator to form a carrier generation layer. Thickness of this tin film about 0.2 μ.

Then, a carrier transport layer was formed in the same manner as in Example 1 using the compounds shown in Table 2 to obtain double-layer type photoreceptors. These photoreceptors were evaluated under the same measuring conditions as in Example 1. The results are shown in Table 2.

TABLE 2

| Compound | The 1st time | | The 1000th time | |
|---|---|---|---|---|
| | $V_0$ (volt) | E1/2 (lux · sec) | $V_0$ (volt) | E1/2 (lux · sec) |
| (3) | −960 | 1.4 | −950 | 1.4 |
| (8) | −860 | 1.4 | −850 | 1.4 |
| (12) | −910 | 1.5 | −910 | 1.5 |
| (28) | −880 | 1.6 | −860 | 1.6 |
| (35) | −940 | 1.3 | −930 | 1.3 |
| (40) | −850 | 1.4 | −850 | 1.4 |
| (50) | −900 | 1.5 | −880 | 1.5 |
| (60) | −910 | 1.5 | −900 | 1.5 |

As explained above, according to the present invention, an electrophotographic photoreceptor can be obtained which has high sensitivity and high endurance.

What is claimed is:

1. An electrophotographic photoreceptor which comprises an electroconductive support and, provided thereon, a photosensitive layer which contains a compound represented by the following formula [I]:

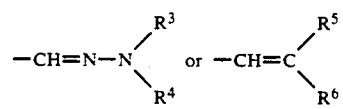

[I]

wherein $R^1$ and $R^2$ each represents a hydrogen atom or an alkyl, aralkyl or aryl group which may have substituent: X represents

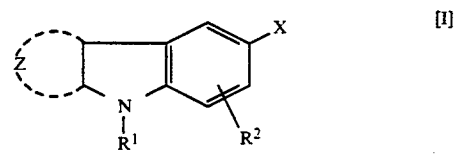

in which $R^3$ and $R^4$ each represents an alkyl, aralkyl or aryl group which may have substituent and $R^5$ and $R^6$ each represents a hydrogen atom or an alkyl, aralkyl or aryl group which may have substituent and $R^5$ and $R^6$ may link to each other to form a ring; and Z represents a group of atoms necessary for forming a saturated 5-8 membered ring together with two carbon atoms of the indoline ring.

2. A photoreceptor according to claim 1, wherein the compound is a hydrazone compound represented by the following formula [I']:

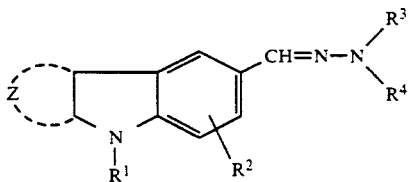

wherein $R^1$, $R^2$, $R^3$, $R^4$ and Z are the same as defined above.

3. A photoreceptor according to claim 1, wherein the compound is a styryl compound represented by the following formula [I'']:

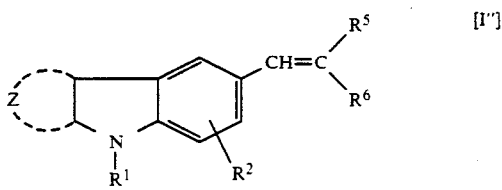

wherein $R^1$, $R^2$, $R^5$, $R^6$ and Z are the same as defined above.

4. A photoreceptor according to claim 1, wherein the photosensitive layer contains the compound represented by the formula [I] dissolved or dispersed in a binder resin.

5. A photoreceptor according to claim 1, wherein the photosensitive layer contains the compound represented by the formula [I] and a carrier generation material.

6. A photoreceptor according to claim 1, wherein the photosensitive layer comprises a carrier generation layer and a carrier transport layer, said carrier transport layer containing the compound represented by the formula [I].

7. A photoreceptor according to claim 6, which has the carrier generation layer on the support and the carrier transport layer on the carrier generation layer.

8. A photoreceptor according to claim 4, wherein amount of the binder resin is 0.2–10 times the weight of the compound represented by the formula [I].

9. A photoreceptor according to claim 8, wherein the amount of the binder resin is 0.5–5 times the weight of the compound represented by the formula [I].

10. A photoreceptor according to claim 1, wherein the electroconductive support is selected from metal drum, metal sheet and sheet-like, drum-like and belt-like paper and plastic film subjected to electroconductive treatment.

* * * * *